United States Patent
Wang et al.

(10) Patent No.: US 7,208,625 B1
(45) Date of Patent: Apr. 24, 2007

(54) REMOVING PERMANGANATE-REDUCING IMPURITIES FROM ACETIC ACID

(75) Inventors: Wei Wang, Boothwyn, PA (US); Shao-Hua Guo, Exton, PA (US)

(73) Assignee: Lyondell Chemical Technology, L.P., Greenviile, DE (US)

( * ) Notice: Subject to any disclaimer, the term of this patent is extended or adjusted under 35 U.S.C. 154(b) by 0 days.

(21) Appl. No.: 11/499,551

(22) Filed: Aug. 4, 2006

(51) Int. Cl.
*C07C 51/42* (2006.01)

(52) U.S. Cl. ...................................... 562/608
(58) Field of Classification Search ................ 562/608
See application file for complete search history.

(56) References Cited

U.S. PATENT DOCUMENTS

| | | | |
|---|---|---|---|
| 3,769,329 A | 10/1973 | Paulik et al. ............ 260/488 K |
| 5,155,265 A | 10/1992 | Scates et al. ................ 562/608 |
| 5,155,266 A | 10/1992 | Scates et al. ................ 562/608 |
| 5,202,481 A | 4/1993 | Scates et al. ................ 562/608 |
| 5,362,365 A * | 11/1994 | Niijima et al. ................ 203/31 |
| 5,371,286 A | 12/1994 | Blay et al. ................... 562/519 |
| 5,387,713 A | 2/1995 | Cook et al. ................. 562/608 |
| 5,625,095 A | 4/1997 | Miura et al. ................. 562/519 |
| 5,783,731 A | 7/1998 | Fisher et al. ................. 562/519 |
| 5,817,869 A | 10/1998 | Hinnenkamp et al. ...... 562/519 |
| 6,143,930 A | 11/2000 | Singh et al. ................. 562/608 |
| 6,232,491 B1 | 5/2001 | Cunnington et al. ........ 560/248 |
| 6,323,364 B1 | 11/2001 | Agrawal et al. ............. 562/519 |
| 6,339,171 B1 | 1/2002 | Singh et al. ................. 562/519 |
| 6,416,237 B2 | 7/2002 | Lissotschenko et al. ...... 385/88 |
| 6,667,418 B2 * | 12/2003 | Broussard et al. ........... 562/519 |

FOREIGN PATENT DOCUMENTS

JP 61056151 A * 3/1986

* cited by examiner

*Primary Examiner*—Thurman K. Page
*Assistant Examiner*—MLouisa Lao
(74) *Attorney, Agent, or Firm*—Shao-Hua Guo

(57) ABSTRACT

A method for removing permanganate-reducing impurities from an acetic acid product is disclosed. The method comprises contacting an acetic acid product containing permanganate-reducing impurities with peracetic acid and an oxygen-containing gas. The method is particularly suitable for post treatment of acetic acid that contains permanganate-reducing impurities such as crotonaldehyde.

16 Claims, No Drawings

REMOVING PERMANGANATE-REDUCING IMPURITIES FROM ACETIC ACID

FIELD OF THE INVENTION

The invention relates to purification of acetic acid. More particularly, the invention relates to removing permanganate-reducing impurities from acetic acid.

BACKGROUND OF THE INVENTION

The carbonylation of methanol produces acetic acid:

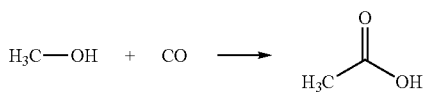

Prior to 1970, acetic acid was made using cobalt catalysts. A rhodium carbonyl iodide catalyst was developed in 1970 by Monsanto. The rhodium catalyst is considerably more active than the cobalt catalyst, which allows lower reaction pressure and temperature. Most importantly, the rhodium catalyst gives high selectivity to acetic acid.

One problem with the original Monsanto process is that a large amount of water (about 14%) is needed to produce hydrogen in the reactor via the water-gas shift reaction ($CO+H_2O=CO_2+H_2$). Water and hydrogen are needed to react with precipitated Rh(III) and inactive $[RhI_4(CO)_2]^-$ to regenerate the active Rh(I) catalyst. The large amount of water increases the amount of hydrogen iodide needed, which is highly corrosive and leads to engineering problems. Further, removing a large amount of water from the acetic acid product is costly.

In the late '70s, Celanese modified the Monsanto process by the adding lithium iodide salt to the carbonylation. Lithium iodide salt increases the catalyst stability by minimizing the side reactions that produce inactive Rh(III) species and therefore the amount of water needed is reduced. However, the high concentration of lithium iodide salt promotes stress crack corrosion of the reactor vessels. Furthermore, the use of iodide salts increases the iodide impurities in the acetic acid product.

In the late '90s, Lyondell Chemical Company (by its predecessors) developed a new rhodium carbonylation catalyst system that does not use iodide salt. The catalyst system uses a pentavalent Group VA oxide such as triphenylphosphine oxide as a catalyst stabilizer. The Lyondell catalyst system not only reduces the amount of water needed but also increases the carbonylation rate and acetic acid yield. See U.S. Pat. No. 5,817,869.

One challenge still facing the industry is that lowering water concentration in the methanol carbonylation results in increased formation of aldehydes and other permanganate-reducing impurities. For certain applications, acetic acid must pass permanganate time test. Therefore, efforts have been made to remove these impurities from acetic acid product.

U.S. Pat. No. 6,667,418 discloses a method for producing acetic acid by the catalytic carbonylation of methanol to obtain a reaction product stream comprising acetic acid and a minor amount of acetaldehyde. The acetaldehyde content in the reaction product stream is reduced by oxidation to convert at least a portion of the acetaldehyde in the stream to acetic acid or further to $CO_2$ and $H_2O$. The oxidized stream is then directed to the purification section, the reaction section, or both whereby the concentration of acetaldehyde is reduced.

U.S. Pat. No. 6,143,930 discloses a method to manufacture high purity acetic acid by reducing acetaldehyde from a light phase of an intermediate stream in the reaction process by employing a multiple distillation process coupled with an optional extraction of acetaldehyde. The distillation process involves first distilling a light phase to concentrate the acetaldehyde, and then separating it in a second distillation tower. The second distillation serves to remove acetaldehyde from methyl iodide, methyl acetate, and methanol mixture. As an optional third step, the twice distilled stream may be directed to an extractor to remove any remaining quantities of methyl iodide from the aqueous acetaldehyde stream to obtain acetic acid as a final product in greater than 99% purity.

U.S. Pat. No. 5,783,731 discloses a process to reduce carbonyl impurities in a carbonylation reaction for the production of acetic acid. The methyl iodide recycle stream, which is directed to a carbonylation reactor for carbonylating methanol or methyl acetate to acetic acid, is treated to remove aldehyde impurities by reacting the methyl iodide stream formed in the reaction with an aqueous amino compound which reacts with the aldehydes to form water soluble nitrogenous derivatives, separating an organic methyl iodide phase from an aqueous derivative phase and distilling the methyl iodide phase to remove heavier impurities.

U.S. Pat. No. 5,155,266 discloses a method for improving the permanganate time of acetic acid produced by the low water carbonylation of methanol in a reaction medium comprising methanol, carbon monoxide, from 0.5% to 30 wt % of methyl acetate, from 5% to 20 wt % of methyl iodide, from 20% to 20 wt % of soluble alkali metal iodide, and a halogen-promoted rhodium catalyst in the presence of less than 14 wt % of water. The method comprises contacting said acid with ozone in the presence of an oxidation catalyst.

All above known methods are necessarily performed in an integrated acetic acid production process. They require the use of complicated distillation equipment and oxidizing agents such as peroxides and ozone. Therefore, these methods are not suitable for the post-treatment acetic acid product which has been made.

New method for removing aldehyde and other permanganate-reducing impurities from acetic acid product is needed. Ideally, the method could be performed conveniently and effectively.

SUMMARY OF THE INVENTION

The invention is a method for purification of acetic acid product. The method comprises contacting an acetic acid product which contains a permanganate-reducing impurity with peracetic acid and an oxygen-containing gas. We surprisingly found that the coexistence of peracetic acid and oxygen significantly enhances the purification. The method is effective even at a low concentration of peracetic acid and at an ambient temperature. Peracetic acid oxidizes the permanganate-reducing impurities. For instance, peracetic acid reacts with acetaldehyde and forms acetic acid. The method of the invention is suitable for post treatment of acetic acid product because it can be performed at mild conditions such as in storage vessels and does not introduce foreign impurities that might require additional separation.

DETAILED DESCRIPTION OF THE INVENTION

Acetic acid is commonly produced by methanol carbonylation. The carbonylation reaction is performed in the presence of a carbonylation catalyst such as rhodium catalyst and iridium catalyst. Permanganate-reducing impurities such as ketones, aldehydes, and olefins are formed during the carbonylation. By "olefins," we mean compounds containing C=C double bonds. For instance, acetic acid can be reduced by hydrogen in the presence of carbon monoxide and rhodium catalyst to form acetaldehyde. Acetaldehyde can also be formed from hydrogenolysis of the rhodium-acyl intermediate. An aldol condensation of acetaldehyde produces crotonaldehyde. Through its C=C double bond, crotonaldehyde can continue to react and to form butyraldehyde and 2-ethyl crotonaldehyde.

The boiling point of acetaldehyde is 21° C., while the boiling point of acetic acid is 118° C. Acetaldehyde is thus relatively easy to separate from acetic acid by distillation. Crotonaldehyde has a boiling point of 101° C., and it is relatively difficult to remove from acetic acid. Furthermore, aldehyde impurities are formed not only during the carbonylation reaction but also during distillation of acetic acid. Therefore, acetic acid products are often not free of aldehyde impurities. The prior art methods have been focused on the removal of acetaldehyde during the acetic acid production process. In contrary, the method of the invention is particularly useful for removing crotonaldehyde after the acetic acid product is produced.

The method of the invention comprises contacting an acetic acid product containing a permanganate-reducing impurity with peracetic acid and an oxygen-containing gas. We surprisingly found that the coexistence of peracetic acid and an oxygen-containing gas makes the removal of the permanganate-reducing impurities much more efficient than the use of peracetic acid alone. The high efficiency of the method of the invention makes it possible to remove permanganate impurities from acetic acid under mild conditions.

Preferably, the method of the invention is performed at a temperature below the boiling point of acetic acid (118° C.). More preferably, the method of the invention is performed at a temperature lower than or equal to 65° C. Most preferably, the method of the invention is performed at a temperature lower than or equal to 45° C. One advantage of the invention is that the method can be performed at an ambient temperature (for instance 15°–35° C.). It can be performed in a storage vessel.

As discussed above, the method of the invention is particularly suitable for post treatment of acetic acid product, although it can also be performed in any stage of the acetic acid production process. For instance, it can be performed in the so-called "light ends distillation," "drying distillation," or "heavy ends distillation." Light ends distillation is a distillation which separates the lights such as methyl acetate and methyl iodide from the acetic acid product. Drying distillation is a distillation which separates water from the acetic acid product of the light ends distillation. Heavy ends distillation is a distillation which separates heavy impurities such as propionic acid from the acetic acid product of the drying distillation. The method of the invention can be performed in the so-called "combined" distillation. A combined distillation is a distillation which combines the light ends distillation and drying distillation in a single column.

Suitable oxygen-containing gas includes oxygen, air, and mixtures of oxygen with an inner gas such as carbon dioxide and nitrogen. Air is particularly preferred. Preferably, the oxygen-containing gas is bubbled through the acetic acid product during the treatment. Alternatively, the acetic acid can be saturated with the oxygen-containing gas, and peracetic acid is then added to the acetic acid.

Peracetic acid can be pure or in solution. Preferably, the peracetic acid is an aqueous solution or a solution in acetic acid. When the peracetic acid is an aqueous solution, a high peracetic acid concentration is preferred. Peracetic acid oxidizes the permanganate-reducing impurities and the peracetic acid is reduced to acetic acid. Thus, one advantage of the invention is that no foreign impurities are necessarily introduced to the acetic acid product by the treatment.

The amount of peracetic acid used depends on the nature and the concentration of the permanganate-reducing impurities. Preferably, peracetic acid is used in an amount within the range of about 0.1 to about 1,000 equivalents per equivalent of the permanganate-reducing impurities. More preferably, peracetic acid is used in an amount within the range of 0.1 to about 10 equivalents per equivalent of the permanganate-reducing impurities. Most preferably, peracetic acid is used in an amount within the range of 0.5 to 5.0 equivalents per equivalent of the permanganate-reducing impurities. One advantage of the invention is that peracetic acid can be used in less than or equal to one equivalent per equivalent of the permanganate-reducing impurities so that no significant amount of peracetic acid resides in the treated acetic acid product. An "equivalent of the permanganate-reducing impurities" means the number of moles of peracetic acid theoretically needed to react with one mole of the permanganate-reducing impurity. For instance, one mole of acetaldehyde needs one mole of peracetic acid to be oxidized; while one mole of crotonaldehyde needs five moles of peracetic acid to be completely oxidized.

The following examples merely illustrate the invention. Those skilled in the art will recognize many variations that are within the spirit of the invention and scope of the claims.

Permanganate Time Test

A potassium permanganate solution is added into acetic acid sample to find reducing agents such as acetaldehyde in the sample by the time for fading any of the pink color of potassium permanganate. A standard permanganate solution is used as reference to determine the end point. The test is carried out at 15±0.5° C. The concentration of potassium permanganate solution is 1.0 g/L. The test sample is prepared by mixing 5 mL of acetic acid sample, 15 mL of distilled water and 1 mL of potassium permanganate solution (1.0 g/L) in a color comparison tube. The test tube is put into a thermostatic water bath which is controlled at 15±0.5° C. The reference standard solution prepared by mixing 0.8 mL potassium permanganate solution and 20 mL water is also put into the thermostatic water bath. The color of the test sample is compared against reference standard solution. If there is no color difference between test sample and reference standard solution in 2 hours at 15° C., the acetic acid passes the test; if there is any pink color fading compared to the reference standard solution, the acetic acid sample fails the test.

EXAMPLE 1

Treatment with Peracetic Acid and Air

Two hundred grams of acetic acid containing 10 ppm of acetaldehyde is mixed with 0.0432 gram of peracetic acid solution in acetic acid (32%, product of Aldrich) in a glass container. The molar ratio of peracetic acid to acetaldehyde is 4:1. The mixture is bubbled with air for 15 minutes and then sealed. The treatment is carried out at room temperature (about 20° C.). The sample is tested by the Permanganate Time Test described above periodically. After 2 days of treatment, the sample passes the test.

EXAMPLE 2

Treatment with Peracetic Acid and Air

Two hundred grams of acetic acid containing 10 ppm of acetaldehyde is mixed with 0.0108 gram of peracetic acid solution in acetic acid (32%, product of Aldrich) in a glass container. The molar ratio of peracetic acid to acetaldehyde is 1:1. The mixture is bubbled with air for 15 minutes and then sealed. The treatment is carried out at room temperature (about 20° C.). After 5 days of treatment, the sample passes the test.

EXAMPLE 3

Treatment with Peracetic Acid and Air

Four hundred grams of acetic acid containing 10 ppm of acetaldehyde is mixed with 0.0108 gram of peracetic acid solution in acetic acid (32%) in a glass container. The molar ratio of peracetic acid to acetaldehyde is 0.5:1. The mixture is bubbled with air for 15 minutes and then sealed. The treatment is carried out at room temperature (about 20° C.). After 5 days of treatment, the sample passes the Permanganate Time Test.

COMPARATIVE EXAMPLE 4

Treatment with Only Peracetic Acid

Two hundred grams of acetic acid containing 10 ppm acetaldehyde is mixed with 0.0432 gram of peracetic acid solution in acetic acid (32%) in a glass container. The molar ratio of peracetic acid to acetaldehyde is 4:1. The treatment is carried out at room temperature (about 20° C.). The sample still fails the Permanganate Time Test after 6 days of treatment.

COMPARATIVE EXAMPLE 5

Treatment with Only Peracetic Acid

Four hundred grams of acetic acid containing 10 ppm of acetaldehyde is mixed with 0.0108 gram of peracetic acid solution in acetic acid (32%) in a glass container. The molar ratio of peracetic acid to acetaldehyde is 0.5:1. The treatment is carried out at room temperature (about 20° C.). The treatment sample still fails the Permanganate Time Test after 6 days of treatment.

COMPARATIVE EXAMPLE 6

Treatment with Only Air

Two hundred grams of acetic acid containing 10 ppm of acetaldehyde is added to a glass container. The acetic acid is bubbled with air for 15 minutes and then the container is sealed. The treatment is carried out at room temperature (about 20° C.). The sample still fails the Permanganate Time Test after 6 days of the treatment.

COMPARATIVE EXAMPLE 7

Treatment with Hydrogen Peroxide and Air

Four hundred grams of acetic acid containing 10 ppm of acetaldehyde is mixed with 0.0412 gram of hydrogen peroxide aqueous solution (30%, product of Aldrich) in a glass container. The molar ratio of hydrogen peroxide to acetaldehyde is 4:1. The mixture is bubbled with air for 15 minutes and then sealed. The treatment is carried out at room temperature (about 20° C.). The sample still fails the Permanganate Time Test after 6 days of treatment.

TABLE 1

Summary of Treatment Results

| Ex. No. | Treatment Method | Peracetic acid/ acetaldehyde (molar ratio) | $H_2O_2$/ Acetaldehyde (molar ratio) | Treatment Time (day) | Permanganate time test results |
|---|---|---|---|---|---|
| 1 | Peracetic acid and air | 4:1 | — | 2 | pass |
| 2 | Peracetic acid and air | 1:1 | — | 5 | pass |
| 3 | Peracetic acid and air | 0.5:1 | — | 5 | pass |
| C4 | Peracetic acid | 4:1 | — | 6 | fail |
| C5 | Only Peracetic acid | 0.5:1 | — | 6 | fail |
| C6 | Only Air | — | — | 6 | fail |
| C7 | $H_2O_2$ and air | — | 4:1 | 6 | fail |

We claim:

1. A method for purifying an acetic acid containing a permanganate-reducing impurity, said method consisting essentially of contacting the acetic acid with peracetic acid and air.

2. The method of claim 1, wherein the permanganate-reducing impurity is selected from the group consisting of ketones, aldehydes, olefins, and mixtures thereof.

3. The method of claim 1, wherein the permanganate-reducing impurity is an aldehyde.

4. The method of claim 3, wherein the aldehyde is selected from the group consisting of acetaldehyde, crotonaldehyde, butyraldehyde, 2-ethylcrotonaldehyde, 2-ethylbutyraldehyde, and mixtures thereof.

5. The method of claim 1, wherein the permanganate-reducing impurity is crotonaldehyde.

6. The method of claim 1, wherein air is air.

7. The method of claim 1, wherein the acetic acid product is mixed with peracetic acid and air is then bubbled through the mixture.

8. The method of claim 1, wherein the acetic acid product is saturated with air and is then mixed with peracetic acid.

9. The method of claim 1, wherein the acetic acid is contacted with the peracetic acid and air a temperature lower than 118° C.

10. The method of claim 1, wherein the acetic acid is contacted with the peracetic acid and air at a temperature of 65° C. or lower.

11. The method of claim 1, wherein the acetic acid is contacted with the peracetic acid and air at a temperature of 45° C. or lower.

12. The method of claim 1, which is performed in a storage vessel for the acetic acid product.

13. The method of claim 1, wherein the peracetic acid is present in an amount within the range of 0.1 to 1,000 equivalents per equivalent of the permanganate-reducing impurity.

14. The method of claim 1, wherein the peracetic acid is present in an amount within the range of 0.1 to 10 equivalents per equivalent of the permanganate reducing impurity.

15. The method of claim 1, wherein the peracetic acid is present in an amount within the range of 0.5 to 5 equivalents per equivalent of the permanganate-reducing impurity.

16. The method of claim 1, wherein the peracetic acid is present in an amount within the range of 0.5 to 1 equivalent per equivalent of the permanganate-reducing impurity.

* * * * *